(12) United States Patent
Rafiee et al.

(10) Patent No.: US 8,524,211 B1
(45) Date of Patent: Sep. 3, 2013

(54) VEGETABLE SOURCED PETROLATUM COSMETIC

(75) Inventors: Lara Marie Rafiee, Trumbull, CT (US); Michael Charles Cheney, Trumbull, CT (US); Brian John Dobkowski, Trumbull, CT (US); Vivek Subramanian, Trumbull, CT (US); Qian Wang, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/477,337

(22) Filed: May 22, 2012

(51) Int. Cl.
*A61K 31/74* (2006.01)
(52) U.S. Cl.
USPC ...................................... 424/78.03
(58) Field of Classification Search
None
See application file for complete search history.

(56) References Cited

U.S. PATENT DOCUMENTS

| 7,351,417 B2 | 4/2008 | Barrow et al. |
| 2004/0120909 A1 | 6/2004 | Lee et al. |
| 2007/0224142 A1 | 9/2007 | Swaile et al. |

FOREIGN PATENT DOCUMENTS

JP  2010275201 A  12/2010

OTHER PUBLICATIONS http://en.wikipedia.org/wiki/Polyglycerol_polyricinoleate.*
"GRAS Notice 000270: polyricinoleic acid" (PDF). http://www.accessdata.fda.gov/scripts/fcn/gras_notices/grn000270.pdf. 2008.*

* cited by examiner

*Primary Examiner* — Carlos Azpuru
(74) *Attorney, Agent, or Firm* — Rimma Mitelman

(57) ABSTRACT

A cosmetic composition is provided which includes a triglyceride, a castor oil, glycerin, and a polyglyceryl ricinoleate. The composition is a vegetable sourced alternative to petrolatum and has been found to be an excellent moisturizing composition and delivering good skinfeel properties and lustre to skin.

11 Claims, No Drawings

VEGETABLE SOURCED PETROLATUM COSMETIC

BACKGROUND OF THE INVENTION

1. Field of the Invention

The invention concerns a vegetable based mimic of petrolatum which achieves improved skinfeel aesthetics and imparts to skin a healthy lustre.

2. The Related Art

The petrolatum which is commercially available under the Vaseline® brand is an occlusive substance. When placed on skin, the substance prevents moisture evaporation. Retention of the moisture promotes healing and controls cracking/flaking occurring under cold weather conditions.

Unfortunately, petrolatum imparts a greasy feel to the formulations. Further, petrolatum containing substances are not easily formulated to provide good lustre when applied to skin.

U.S. Patent Application Publication No. 2007/0224142 A1 (Swaile et al.) describe hydrogenated castor oil based compositions as replacements for petrolatum. These compositions are deodorants formulated as aqueous or anhydrous systems to be effective at preventing or eliminating malodors resulting from perspiration. Besides hydrogenated castor oil, the compositions include thickening or structuring agents such as 12-hydroxystearic acid and derivatives thereof, alcohol liquid carriers such as glycerin and polyglycerols, and usually a significant amount of water. Although the compositions are reported useful for deodorancy, there is no indication of any improved skinfeel properties or lustre relative to petrolatum containing formulations.

SUMMARY OF THE INVENTION

A cosmetic composition is provided which includes:
(i) from about 10 to about 60% by weight of a triglyceride;
(ii) from about 5 to about 40% by weight of a castor oil;
(iii) from 10 to 50% by weight of glycerin; and
(iv) from about 0.5 to about 10% by weight of a polyglyceryl ricinoleate.

DETAILED DESCRIPTION OF THE INVENTION

Now it has been found that vegetable based compositions can impart to skin good lustre and skinfeel aesthetics. The compositions require a combination of a triglyceride, glycerin, a castor oil, and a polyglyceryl ricinoleate.

A first component of the present invention is that of a triglyceride. Typical triglycerides include caprylic/capric triglyceride, coconut oil, sunflower seed oil, safflower oil, cottonseed oil, olive oil and mixtures thereof. Particularly useful is caprylic/capric triglyceride and coconut oil, respectively.

Amounts of the triglyceride may range from about 10 to about 60%, preferably from about 20 to about 50%, and optimally from about 30 to about 45% by weight of the composition.

Another component of the present invention is a castor oil, particularly a hydrogenated castor oil, a castor seed oil or combinations thereof. Amounts of the castor oil may range from about 5 to about 40%, preferably from about 10 to about 30%, and optimally from about 15 to about 25% by weight of the composition. For purposes of this invention, a castor oil is not considered a triglyceride.

A further useful component is glycerin, also known as glycerol. Amounts of this material may range from about 10 to about 50%, preferably from about 20 to about 40%, and optimally from about 25 to about 35% by weight of the composition.

A still further component is a polyglyceryl ricinoleate. The number of glycerol repeating units may range from 2 to 20, preferably from 4 to 10, optimally about 6 repeating units. The term "ricinoleate" herein includes mono- and poly-ricinoleate esters of glycerol. When the ricinoleate is in poly form, the number of mono ricinoleate units can range from 2 to 20, particularly from 2 to 5. Most preferred is polyglyceryl-6 polyricinoleate sold by Barnet Products Corp. under the trademark Hexaglyn PR-156 and having an INCI name of Polyglyceryl-6 Polyricinoleate. Amounts of this material may range from about 0.5 to about 10%, preferably from about 1 to about 8%, and optimally from about 4 to about 6% by weight of the composition.

Advantageously present may be a fatty acid material selected from the group consisting of trihydroxystearin, 12-hydroxystearic acid, and combinations thereof. Amounts of these materials, when present, may range from about 0.1 to about 15%, preferably from about 0.5 to about 10%, more preferably from about 2 to about 8%, and optimally from about 3 to about 6% by weight of the composition.

Advantageously, but not necessarily, the compositions will be anhydrous. By the term "anhydrous" is meant a water presence from 0 to 5%, preferably from 0 to 2%, and optimally 0% by weight of the composition.

Another useful but adjunct component of the present invention is an emulsifier such as lecithin. Amounts of the lecithin may range from about 0.01 to about 2%, preferably from about 0.1 to about 1%, and optimally from about 0.3 to about 0.8% by weight of the composition.

Sunscreen actives may also be included in compositions of the present invention. Particularly preferred are such materials as ethylhexyl p-methoxycinnamate, available as Parsol MCX®, Avobenzone, available as Parsol 1789® and benzophenone-3, also known as Oxybenzone. Inorganic sunscreen actives may be employed such as microfine titanium dioxide, zinc oxide, polyethylene and various other polymers. Amounts of the sunscreen agents when present may generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain vitamins. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, Ascorbyl Tetraisopalmitate, Vitamin E (tocopherol), Vitamin E Acetate and DL-panthenol. Total amount of vitamins when present in the compositions may range from 0.001 to 10%, preferably from 0.01% to 1%, optimally from 0.1 to 0.5% by weight.

Colorants, fragrances, opacifiers and abrasives may also be included in compositions of the present invention. Each of these substances may range from about 0.05 to about 5%, preferably between 0.1 and 3% by weight.

Advantageously, compositions of the invention may exhibit mean Lustre Values, as measured from a SAMBA Visual Appearance System using a Reich-Robbins assessment, that may range from 3 to 15, or from 3 to 10, or from 6 to 10, and selectively from 7 to 10.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

It should be noted that in specifying any range of concentration or amount, any particular upper concentration can be associated with any particular lower concentration or amount.

The following examples will more fully illustrate the embodiments of this invention. All parts, percentages and proportions referred to herein and in the appended claims are by weight unless otherwise illustrated.

EXAMPLE 1

A series of clinical experiments were conducted to evaluate compositions of this invention against standard petrolatum. The clinical involved 55 panelists in a Moisturization Efficacy Test. The study included a five-day conditioning phase followed by a two-week treatment phase. Effect on the panelists was measured with Skicon, Corneometer and TEWL instruments/methodology. Additionally, expert evaluators did a visual dryness assessment.

The formulas applied to the panelists were those reported in Table I. Performance results against petrolatum as a standard are described under Table II.

The SkiCon Value is measured with a SkiCon 200 instrument. Moisturization is measured on the skin surface through a conductance evaluation (micro Siemens). Depth of measurement is approximately less than 15 μm. The panelists were requested to pre-wash with a standard Ivory® soap. After 30 minutes, the panelists' skin was measured using the SkiCon 200 instrument. A sample of 0.05 gram experimental product was then applied onto a 5×5 cm area marked on an inner forearm. Post-application measurements are taken two hours after the initial treatment.

Corneometry is a method for determining skin hydration. This technique determines the capacitance of skin due to its behavior as a dielectric medium and assesses a 10-20 micron thickness of the stratum corneum. The method utilized a Corneometer 825 meter (Courage-Khazaka Electronics) with a handheld probe.

Another technique utilized for the clinical study was measurement of transepidermal water loss (TEWL) through the epidermal surface. The TEWL value is a measure of the rate of water lost through the skin and is an estimate of the skin's ability to retain moisture. It is an index of possible damage of the skin's water-barrier function. Because water loss through the skin normally occurs by passive diffusion through the epidermis, higher TEWL values indicate greater water loss and are consistent with increased damage. TEWL values were determined using a Tewameter 300 meter (Courage-Khazaka Electronics, Germany).

TABLE I

| Formulas | | | |
|---|---|---|---|
| | Weight % | | |
| Formula | Sample A | Sample B | Sample C |
| Glycerin | 30.00 | 20.00 | 10.00 |
| Castor Oil | 20.00 | 20.00 | 20.00 |
| Caprylic/Capric Triglyceride | 40.50 | 50.50 | 60.50 |
| Trihydroxystearin | — | — | 4.00 |
| 12-Hydroxystearic Acid | 5.00 | 5.00 | — |
| Polyglyceryl Ricinoleate | 5.00 | 5.00 | 5.00 |
| Lecithin | 0.50 | 0.50 | 0.50 |

TABLE II

| Performance Results Against Petrolatum | | | |
|---|---|---|---|
| Samples | SkiCon Corneometer | TEWL | Visual Dryness |
| Sample A | ✓ | ⊙ | ○ |
| Sample B | ✓ | ○ | ○ |
| Sample C | ✓ | ○ | ○ |

✓ means significantly better at all points
⊙ better for at least one time point
○ parity at all time points All three samples were significantly better than petrolatum at all time points for Skicon and Corneometer instrumental measurements. For the visual dryness and TEWL assessments, the Samples were found at least as good as petrolatum.

EXAMPLE 2

A series of formulas were prepared to evaluate physical aesthetics, and particularly whether their skinfeel was smooth or grainy. Components of the formulas are listed in Table III, most being listed by their INCI nomenclature. Aesthetic results are also recorded in Table III.

TABLE III

| | (Weight %) | | | | | | | | |
|---|---|---|---|---|---|---|---|---|---|
| Formula No | 1 | 2 | 3 | 4 | 5 | 6 | 7 | 8 | 9 |
| Glycerin | 30.0 | 30.0 | 30.0 | 30.0 | 30.0 | 30.0 | 30.0 | 30.0 | 30.0 |
| Castor Oil | 20.0 | 20.0 | 61.0 | 61.5 | 60.75 | 46.0 | 20.0 | 20.0 | 20.0 |
| Caprylic/Capric Triglycerides | 40.5 | 40.0 | — | — | — | 15.0 | 40.5 | 40.5 | 40.5 |
| Polyglyceryl-6 Ricinoleate | 5.0 | 4.5 | 4.5 | 5.0 | 3.8 | 4.5 | — | — | — |

TABLE III-continued

| | (Weight %) | | | | | | | | |
|---|---|---|---|---|---|---|---|---|---|
| Formula No | 1 | 2 | 3 | 4 | 5 | 6 | 7 | 8 | 9 |
| Polyglyceryl-3 Diisostearate | — | — | — | — | — | — | 5.0 | — | — |
| Polyglyceryl-3 Dioleate | — | — | — | — | — | — | — | 5.0 | — |
| Polyglyceryl-6 Pentastearate | — | — | — | — | — | — | — | — | 5.0 |
| Trihydroxystearin | 4.0 | 4.0 | 4.0 | — | 2.5 | 4.0 | 4.0 | 4.0 | 4.0 |
| 12-Hydroxy Stearic Acid | — | 1.0 | — | 3.0 | 2.5 | — | — | — | — |
| Lecithin | 0.5 | 0.5 | 0.5 | 0.5 | 0.5 | 0.5 | 0.5 | 0.5 | 0.5 |
| Skinfeel Aesthetics | Smooth | Smooth | Grainy | Grainy | Grainy | Grainy | Grainy | Grainy with Separation | Grainy |

Based on the results reported in Table III, only formulas 1 and 2 were found to be aesthetically acceptable. Formula 3 eliminated the caprylic/capric triglyceride and increased the castor oil by a factor of three. The result was inferior to that of formula 1. The effect of different polyglyceryl fatty esters was explored with formulas 7, 8 and 9. These substituted polyglceryl-3 diisostearate, polyglyceryl-3 dioleate, and polyglyceryl-6 pentastearate respectively for polyglyceryl-6 ricinoleate. Formulas with the diisostearate, dioleate and pentastearate derivatives of polyglyceryl were found aesthetically inferior to polyglyceryl ricinoleate because of graininess.

EXAMPLE 3

Lustre properties were evaluated for the eight formulas reported under Table III.
Methodology
Lustre is a term used to describe the state or quality of shining by reflecting light. Lustre qualifies the visual appearance of the object. Lustre is generally considered to depend on three main parameters:
(a) Amount of reflective light; the more reflected light there is, the higher the lustre.
(b) Distribution/width of reflected light; for a same amount of reflected light, the more defined and more concentrated the reflective light is, the higher the lustre.
(c) Background on which the reflection is observed; the darker the background, the more contrast in the reflection and the higher the lustre.
Amongst several methods of quantifying human perception of lustre is the Reich-Robbins method based on the aforementioned three basic assessments about lustre. The operative formula is:

$$L_{Reich-Robbins} = \frac{S}{D * \theta_{1/2}}$$

wherein:
S is the total amount (integral) of the specular light.
D is the total amount (integral) of the diffused light.
$\theta_{1/2}$ is the width of the specular light distribution.
Shine visual appearance was measured using a SAMBA Visual Appearance System described by N. Lefaudeux, N. Lechocinski, P. Clemenceau, S. Breugnot, "New Luster Formula for the Characterization of Hair Tresses Using Polarization Imaging", *Third Annual Conference on Applied Hair Science*, September 2008.

The SAMBA system is a polarization imaging apparatus which allows physical separation of specular light from diffused light for an imaged sample. The apparatus allows recording of three types of images:
A normal intensity image representing what a human eye would see.
A specular image representing the light that is remaining polarized. This polarized light shows only the reflections on the surface of the sample. These reflections are responsible for the visual sensation of lustre.
A diffused light image representing the light that is unpolarized. This unpolarized light shows only the light scattered from the sample. It is the background color of the sample.
Measurement samples were prepared by applying a 1 mm thick film on a black heavyweight construction paper (Pacon Corp). The paper was then mounted on a cylinder and images were taken by the SAMBA system. Formula numbers correspond to those in Table III and their respective compositions. The $L_{Reich-Robbins}$ mean values are recorded in Table IV.

TABLE IV

| Formula No. | Lustre (Reich-Robbins) Mean | Pair Comparisons Tukey-Cramer HSD* |
|---|---|---|
| 1 | 9.19 | A |
| 2 | 7.39 | A |
| 7 | 5.10 | B |
| 8 | 3.61 | B/C |
| 5 | 2.10 | C/D |
| 6 | 1.89 | C/D |
| 4 | 1.74 | D |
| 3 | 0.85 | D |
| 9 | 0.95 | D |

*Levels not connected by same letter are significantly different.

Highest lustre was exhibited by Formulas 1 and 2. Substitution of the polyglyceryl ricinoleate by other polyglyceryls as in Formulas 7, 8 and 9 reduced visual shine relative to Formulas 1 and 2. Absence of caprylic/capric triglycerides, as in Formulas 3-5 also reduced lustre.

While the invention has been described in detail with reference to specific embodiments thereof, it would be apparent to one of skill in the art that various changes and modifications could be made therein without departing from the spirit and scope thereof.

What is claimed is:
1. A cosmetic composition comprising:
(i) from about 10 to about 60% by weight of a triglyceride;
(ii) from about 5 to about 40% by weight of a castor oil;

(iii) from 10 to 50% by weight of glycerin; and
(iv) from about 0.5 to about 10% by weight of a polyglyceryl ricinoleate.

2. The composition according to claim 1 wherein the polyglyceryl ricinoleate has from to 20 glycerol repeating units.

3. The composition according to claim 1 wherein the polyglyceryl ricinoleate has from 4 to 10 glycerol repeating units.

4. The composition according to claim 1 wherein the polyglyceryl ricinoleate is polyglyceryl-6 ricinoleate.

5. The composition according to claim 1 which is anhydrous.

6. The cosmetic composition according to claim 1 further comprising from about 0.1 to about 15% by weight of a material selected from a group consisting of trihydroxystearin, 12-hydroxystearic acid and combinations thereof.

7. The cosmetic composition according to claim 6 wherein the material is present in an amount from about 3 to about 6% by weight.

8. The cosmetic composition according to claim 1 wherein the polyglyceryl ricinoleate is present from about 1 to about 8% by weight.

9. The cosmetic composition according to claim 1 wherein the glycerin is present from about 20 to about 40% by weight.

10. The cosmetic composition according to claim 1 wherein the triglyceride is caprylic/capric triglyceride.

11. The cosmetic composition according to claim 1 wherein the composition exhibits a mean Lustre Value, as measured from a SAMBA Visual Appearance System using a Reich-Robbins assessment, that ranges from 3 to 15.

* * * * *